United States Patent [19]

Nassar

[11] 4,148,892

[45] Apr. 10, 1979

[54] MALE ORAL CONTRACEPTIVE

[76] Inventor: Michael F. Nassar, 8731 Dewey Dr., Garden Grove, Calif. 92641

[21] Appl. No.: 903,720

[22] Filed: May 8, 1978

[51] Int. Cl.$^2$ ............................................. A61K 35/78
[52] U.S. Cl. .................................................... 424/195
[58] Field of Search ........................................ 424/195

[56] References Cited

PUBLICATIONS

Remington, The Practice of Pharmacy, 3rd Ed., 1895, published by J. B. Lippencott Co., Phila. Pa., pp. 958, 959 and 1192.

J. Chem. Soc., vol. 80, pp. 707–714.
Chemical Abstracts: vol. 57:9919e, vol. 58:5730f, 58:11601e and 2753d (1963), vol. 55:22587 and 52:9159e.
Steinmetz, Codex Vegetabilis (1957) item 416.

Primary Examiner—Donald B. Moyer
Attorney, Agent, or Firm—Knobbe, Martens, Olson, Hubbard & Bear

[57] ABSTRACT

A simple, nontoxic, effective male oral contraceptive is disclosed which directly effects the metabolism of the sperm by causing an acidotic state in the fluid medium surrounding the sperm thereby inhibiting the sperm's activity.

6 Claims, No Drawings

MALE ORAL CONTRACEPTIVE

BACKGROUND OF THE INVENTION

Social scientists recognize that over population is one of the most serious problems which mankind must face and solve. As an example, in the United States the Department of Health, Education and Welfare released statistics recently which showed that 3.3 million babies were born in the United States in 1977, up 5% from the previous year. This marked an increase in the nation's birth rate for the first time since 1970. (1) The problem is even more critical in underdeveloped countries.

In order to control our increasing world population, there exists a myriad of contraceptive devices to prevent unwanted pregnancy.

Each method attempts to achieve a contraceptive possessing the qualities of simplicity, acceptability, efficacy, nontoxicity and absence of adverse side effects. One class of such measures are mechanical contraceptives, such as the diaphragm, which are inserted into the vagina to completely occlude the orifice of the cervix, thus obstructing the migration of spermatozoa upward into the fallopian tubes. Such contraceptives have serious application problems due to the wide variation in size and geometry of the vaginal canal and the cervical opening. These devices often require special insertion instruments and careful fitting, usually by a trained physician. Furthermore, since trained help in application is often necessary, these devices are ill-suited for the underdeveloped countries where they are needed most.

Chemical or spermicidal contraceptives are another well known method for attempting to prevent pregnancy. These devices consist of a carrier agent such as jellies and creams which provide partial obstruction of the cervix and in addition contain nontoxic chemical agents that immobilize sperm. The creams and jellies can be inserted high into the vagina with an applicator or can be encapsulated as capsules or suppositories. Capsules or suppositories are placed in the vagina shortly before coitus to allow sufficient time for them to melt and disperse their active ingredients. However, the use of these devices have resulted in unwanted pregnancies because the spermicidal material is not held for a sufficient length of time (which may be several hours) in the desired location in relation to the cervical opening. As a result of this inability to be effective alone, creams and jellies are often used in conjunction with other contraceptive devices. In addition, suppositories require skill in positioning the device in the depth of the vagina in order to prevent flow back out the vaginal opening.

Another type of mechanical device is the condom, a rubber device that surrounds the penis and contains the sperm after ejaculation. This widely used device suffers from an unnatural or desensitizing feeling to the male and female. In addition, the possibility of a perforation in the sheath and the problem of disposing of spent condoms, make the device less than the ultimate answer to unwanted pregnancy.

Recently, oral contraceptives have gained prominence. The "pill" is a female contraceptive which works by suppressing ovulation. One type of "pill" contains a combination of estrogen and progestogen. The Food and Drug Administration has recently published a brochure which reports that estrogen causes cancer in some animals, but studies have not confirmed that it causes cancer in humans. This brochure also states that the pill doubles a woman's change of having a heart attack as well as increasing the risk of other circulatory problems.

Risk of heart attack is further increased if the woman is a smoker. Pill users who smoke are three times more likely to die of a heart attack than nonsmokers on the pill and ten times more likely than nonsmokers who do not use the pill. (2)

The pill should not be taken by females who have certain ailments. In addition, undesirable side effects will sometimes occur when the female first takes the oral contraceptive. These include nausea and vomiting, increase in breast tenderness and engorgement, accentuation of acne, fluid retention, weight gain, increased vaginal discharge and breakthrough bleeding. Finally, there is documentation to the effect that the risk of death to the user may be on the order of 3 per 100,000. (3)

Given these problems with an oral female contraceptive, much pharmacological research has been focused recently upon producing male oral contraceptives. Alkylating agents and hormones to regulate spermatogenesis and thereby bring about a temporary or controlled sterility have been the subject of experimentation. However, alkylating agents are considered dangerous due to possible irreversible side effects and toxicity. Many unanswered questions remain with the use of hormones also. (4)

Due to the above deficiencies in prior contraceptive methods, recently there has been an attempt to begin discovering new fertility-control agents developed from plant extracts. In the January, 1978, issue of PHARMACEUTICAL TECHNOLOGY, the editors write that:

"In light of evidence that primitive people in certain parts of the world have been able to limit population growth by using plant extracts, the World Health Organization has approved an international program to find new fertility-regulating agents in plants. In 1978, the Department of Pharmacognosy and Pharmacology of the College of Pharmacy at the University of Illinois Medical Center, along with centers in London, Brazil, Hong Kong, South Korea, and Ceylon, will receive funds from WHO for this purpose.

Professor Norman R. Farnsworth, Ph.D., head of the Pharmacognosy and Pharmacology Department, stresses that plants are a key ingredient in our healthcare system: at least 25% of all prescriptions dispensed by community pharmacies contain active principles still extracted from plants. 'Most of these plant drugs,' he says, 'have been discovered by scientists studying folklore uses of plants.' Other University of Illinois projects involve studying published articles on plants for new sources of drugs to treat cancer, pain and high blood pressure."

The invention disclosed is an oral contraceptive formulation which will obviate many of the deficiencies in the prior art. It is the first male oral contraceptive which has proven effectiveness by providing a carefully controllable, temporary sterility, and yet is simple, completely nontoxic, and possesses no side effects.

SUMMARY OF THE INVENTION

The invention is a male oral contraceptive whose active ingredient is an aqueous disiccated extract from a plant, *Ecballium elaterium, Linn*. The active ingredient is extracted from the plant with an acetone, toluene, hexane, absolute alcohol solution, concentrated by column chromatography, dried over a steam bath, desiccated over sulfuric acid, pulverized and mixed with a carrier to produce a contraceptive in the form of a dose for human consumption.

The extraction and concentration process is a sophisticated mechanism which converts a flower of nature, whose value heretofore was only aesthetic, into a drug beneficial to mankind, with a utility to induce controlled temporary sterility in human males.

DESCRIPTION OF THE PREFERRED EMBODIMENT

The plant which provides the active ingredient of the present invention is the Ecballium elaterium, Linn. It inhabits several countries, including the United States, but particularly the middle eastern countries of Lebanon and Syria. It grows exclusively on the rocky mountainous areas. It blossoms in the spring and lasts until the end of September. The flowers are yellow and belong to the composite family and its petals are serrated. Before the claimed invention there was no indication that the flower had any properties which could be useful in contraceptives. Thus, the use of the flower in producing a new contraceptive is highly surprising.

In order to prepare the claimed invention, the plant is collected, dried for two weeks, and the leaves and stem ground up in a mortar and pestle until they become powder. Next follows the extraction of the active ingredient. This extraction is a highly sophisticated process which is necessary in order to isolate and purify the active ingredient into a form which will be suitable for human consumption as a male contraceptive. This extraction and purification process took months of rigorous experimentation to develop and therefore is a significant contribution to the invention. In fact, over 100 experiments were performed in order to perfect the process which will now be described.

Approximately 500 mg. of the powdered plant material is weighed into a 250 ml. volumetric flask and extracted with 50 ml. of a solution consisting of acetone, toluene, hexane, and absolute alcohol for about two hours with the optimum ratios being 14:14:20:12, respectively. The flask is left in a dark box for 24 hours after wrapping it with aluminum foil.

Next, a solution of alcoholic hydroxide is added to the flask, preferably 5 ml. of 40% methanolic potassium hydroxide. The flask is swirled for a few minutes and allowed to stand in the dark for another two hours. The methanol acts as a surfactant with solvent-like properties to extract the necessary pigments. The potassium hydroxide increases the pH and thereby facilitates extraction. The active ingredient is further extracted with an immiscible solvent, preferably 50 ml. of hexane is added to the flask which is then diluted to volume with a high ionic strength salt, preferably a 20% sodium sulfate solution. The sodium sulfate is a base which causes precipitation. The solution is filtered and allowed to stand for another two hours in the dark.

A chromatograhic column 12.5 mm.×30 cm. is assembled with bottom capillary tube 2 mm.×10 cm. extending into the neck of a collecting flask. The column is placed on a filtrator and the bottom is plugged with glass wool. The column is filled with a slurry of silica gel G and hyflo super-cel (1/1 w/w), to about the 20 cm. layer. The slurry is filtered by vacuum and a layer of anhydrous sodium sulfate is then added to the top of the adsorbent and pressed firmly.

10 ml. of the plant solution is added to the column and eluted on the column with flow adjusted at one drop per second. The eluant is a hexane-acetone (94/4) solution. After all the solution is eluted, another layer of adsorbent is added and blended from activated magnesia and diatomaceous earth (1:1 w/w). The eluation is continued with a solution consisting of hexane, methylalcohol and acetone in a ratio of 80:10:10, respectively. The concentrated solution should then be checked on a Beckman DBG spectrophotometer at a wavelength maximum between 470–480 and a split width at 0.03. The reading should be a maximum.

Finally, the solution is dried over a steam bath, desiccated over sulfuric acid for ten days, pulverized, and mixed with a carrier. The large number of suitable excipients which could be used as carrier agents in the present invention are well known to those of ordinary skill in the art. As one embodiment lactose and dicalcium phosphate are used as excipients to form a tablet.

A pharmaceutically active amount of active ingredient is mixed with the carrier. The acceptable range for effectiveness in human males is 1 microgram to 1000 micrograms. In the preferred embodiment, one microgram of active material is mixed with a suitable amount of carrier. The amount of carrier added can be adjusted depending upon the size of table desired. One tablet consisting of a dosage of one microgram of the pharmaceutically active material would have an effectiveness for an 8–12 hour period.

Without attempting to be bound by any particular theory, it is suggested that the temporary and controlled sterility which results from the active ingredients of the claimed invention is produced through the following mechanism. The active ingredient is absorbed and transmitted through the blood to the vesticular tissue such as the epididymis and seminiferous tubules. Sperm are formed in the seminiferous tubules of the testes. Following formation in the seminiferous tubules, the sperm pass through the vasa recta into the epididymis. After the sperm have been in the epididymis for some eighteen hours or more, they mature, develop the power of motility, and thus become capable of fertilizing the ovum.

A small quantity of sperm can be stored in the epididymis, but probably most sperm are stored in the vas deferens. Normally, the sperm in these areas would become motile if released to the exterior. However, the active ingredients of the claimed invention induce the cells surrounding the sperm to secrete carbon dioxide which in the aqueous medium will produce carbonic acid. This production of an acidic state has a direct effect upon the metabolism of the sperm. The sperm's metabolism is greatly increased and thereby activates the sperm to begin utilizing the nutrient substances contained in the fluid surrounding the sperm such as glucose, lactose, glulactose and most of the monosaccharides. This induced hyperactivity of the sperm rapidly depletes the nutrient substances from the surrounding fluid until a point is reached at which the nutrients are essentially exhausted resulting in the complete death of the sperm.

This theory is supported by experimental results which indicated hat the pH of the semen which is normally 7.5 is reduced by the drug to 1.5, thereby dropping the motility of the sperm from the normal level at 95% to 0% and also dropping the number of viable sperms remaining in the ejaculate. Vaginal secretions in the female are quite acidic in nature (pH of 3.5 to 4.0)

and through the action of the active ingredients the semenal fluid would decrease this pH even further rather than neutralizing it as it would in the normal state. Tests conducted on samples from subject's tested 24 hours after taking the capsule showed that the semenal fluid returns to normal.

The contraceptive of the claimed invention possesses no toxic or side effects. Pharmacological tests, such as the pyrogen, histamine-like effect, pressor-like effect and tests for undue toxicity all reported negative results.

The following working and experimental examples provide further insights into the experimental mechanism and conclusively prove the effectiveness of the claimed invention.

EXPERIMENT I

A random sample of mature male rabbits were used in this study. They were given a capsule containing 1 mg. of the test material with some lactose and dicalcium phosphate as excipients, through a gastric tube. One hour after the capsule was injected, those rabbits that did not ejaculate spontaneously were mechanically stimulated, and the ejaculate was collected in a small test tube, and the following results were obtained:

Table 1:

| Normal values of the rabbit's ejaculate. | |
|---|---|
| Amount | 0.02–0.05 ± 0.001 ml. |
| Number | 2000–3500 / cc |
| Motility | 85–98% in first hour |
| | 75–55% in second hour |
| | 50–25% in third hour |
| | 25–5% in fourth hour |
| Morphology | 100% normal forms |
| pH 6.2 ± 0.05 | |

Table 2:

| One hour after taking the capsule. | |
|---|---|
| Amount | 0.02–0.5 ± 0.001 ml. |
| Number | 2000–35000 / cc |
| Motility | 15–2% in first hour |
| | 0% in second hour |
| Morphology | 90–100% normal forms |
| pH | 1.4 ± 0.01 |

Twenty-four hours later the values returned back to normal.

EXPERIMENT 2

In-vitro studies were conducted on the frozen ox semen, which when mixed with the test powder, showed complete liquification with 90% drop in motility.

EXPERIMENT 3

A random sample of men of various nationalities were selected with ages ranging between 18–40 years. Samples of their semen were collected, as a control. One hour after injestion of the capsule containing 1 mg. of the test powder with the excipients, the following results were obtained:

Table 3:

| Normal values of the man's ejaculate. | |
|---|---|
| Amount | 2–4 ml. |
| Number | 80,000,000–120,000,000 / cc |
| Motility | 80–95% in first hour |
| | 80–55% in second hour |
| | 55–35% in third to eighth hour |

Table 3:-continued

| Normal values of the man's ejaculate. | |
|---|---|
| | 35–15% in eighth to fourteenth hour |
| Morphology | 85–95% normal forms |
| pH | 7.2–7.6 ± 0.05 |

After taking the capsule by one hour, another sample from the same subjects were tested.
The average results were as follows:

Table 4:

| One hour after taking the capsule. | |
|---|---|
| Amount | 2–4 ml. |
| Number | 5,000,000–15,000,000 / cc |
| Motility | 25–35% in first hour |
| | 25–5% in second hour |
| | 5–9% in third hour |
| Morphology | 85–95% normal forms |
| pH | 1.5–2.0 ± 0.05 |

Twenty-four hours later, all the values were back to normal.

Various experiments were conducted with samples varying in concentrations between one microgram and one milligram and all concentrations were proven to be effective.

References

1. Los Angeles Times, p. 26, Friday, March 24, 1978.
2. Los Angeles Herald Examiner, p. A-6, Monday, April 3, 1978.
3. Boyd, W., A Textbook of Pathology, Structure and Function in Disease, 8th Ed., pp. 967–1006, 1974.
4. Van Nostrand's Scientific Encyclopedia, 5th Ed., p. 661.

The claimed invention is:
1. A method for preparing a male oral contraceptive containing an active ingredient comprising the steps of
   (a) extracting the active ingredient from the plant, Ecballium elaterium, Linn, with a solution of acetone, toluene, hexane and absolute alcohol;
   (b) adding a solution of alcoholic potassium hydroxide to the extract solution;
   (c) further extracting for the active ingredient with an immiscible solvent;
   (d) diluting to a predetermined volume with high ionic strength salt solution;
   (e) concentrating the active ingredient from the extract solution by column chromatography;
   (f) disiccating the concentrated solution;
   (g) mixing the isolated active ingredient with a carrier in the form of a dose for human consumption.
2. The product produced by the process of claim 1.
3. A method for preventing conception by orally administering to human males the product of claim 2.
4. An oral contraceptive in dosage unit form comprising, per dosage unit a pharmaceutically-effective, non-toxic amount within the range from about 1 to about 1000 micrograms of an active ingredient extracted from the leaves and stem of the plant Ecballium elaterium, Linn, and a pharmaceutical carrier.
5. The contraceptive of claim 4 in table form.
6. A method of preventing conception comprising orally administering to human males a dosage unit in a pharmaceutically-effective, non-toxic amount within the range of from about 1 to about 1000 micrograms of an active ingredient extracted from the leaves and stem of the plant Ecballium elaterium, Linn, mixed with a pharmaceutical carrier.

* * * * *